United States Patent
Miller et al.

(10) Patent No.: US 6,669,638 B1
(45) Date of Patent: Dec. 30, 2003

(54) IMAGING ULTRASOUND TRANSDUCER TEMPERATURE CONTROL SYSTEM AND METHOD

(75) Inventors: David Miller, Woburn, MA (US); Ivan Salgo, Andover, MA (US); Michael Peszynski, Newburyport, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/268,207

(22) Filed: Oct. 10, 2002

(51) Int. Cl.[7] .................................................. A61B 8/00
(52) U.S. Cl. ..................................................... 600/438
(58) Field of Search ................................. 600/407–471; 607/102, 22; 601/2, 3, 159, 169; 604/22

(56) References Cited

U.S. PATENT DOCUMENTS

| | | | | |
|---|---|---|---|---|
| 4,638,436 A | * | 1/1987 | Badger et al. ............... | 607/102 |
| 5,213,103 A | | 5/1993 | Martin et al. .......... | 128/660.01 |
| 5,555,887 A | | 9/1996 | Fraser et al. ........... | 128/663.01 |
| 5,560,362 A | | 10/1996 | Sliwa, Jr. et al. ....... | 128/660.03 |
| 5,721,463 A | | 2/1998 | Snyder ....................... | 310/334 |
| 6,001,069 A | * | 12/1999 | Tachibana et al. ............. | 601/2 |
| 6,050,943 A | | 4/2000 | Slayton et al. | |
| 6,210,356 B1 | | 4/2001 | Anderson et al. ............. | 604/22 |
| 6,500,121 B1 | | 12/2002 | Slayton et al. | |

* cited by examiner

*Primary Examiner*—Ali M. Imam
(74) *Attorney, Agent, or Firm*—John Vodopia (57) ABSTRACT

A system and method for controlling the heat of an ultrasonic transducer is disclosed. The presently preferred embodiments of the present invention control the temperature of the transducer face by changing the imaging modes of the system. In a preferred embodiment, feedback from temperature sensing elements placed in the transducer is used to determine when to switch from a higher power imaging mode to a lower power imaging mode. In another preferred embodiment, the system switches from a higher power imaging mode to a lower power imaging mode after a predetermined period of time has elapsed. In yet another preferred embodiment, the system switches to a "mixed" imaging mode, where the system cycles rapidly between a higher power imaging mode and a lower power imaging mode, and the resulting data is combined to form a single image.

21 Claims, 7 Drawing Sheets

IMAGING ULTRASOUND TRANSDUCER TEMPERATURE CONTROL SYSTEM AND METHOD

BACKGROUND OF THE INVENTION

1. Field of the Invention

The invention relates generally to the field of imaging ultrasonic medical transducer assemblies, and, specifically, to an apparatus and method for cooling the transducer.

2. Description of the Related Art

Imaging ultrasonic medical transducers are used to observe the internal organs of a patient. The ultrasonic range is described essentially by its lower limit: 20kHz, roughly the highest frequency a human can hear. The medical transducers emit ultrasonic pulses which echo (i.e., reflect), refract, or are absorbed by structures in the body. The reflected echoes are received by the transducer and these received signals are translated into images. Such translation is possible because the reflections from the internal organs vary in intensity according to the "acoustic impedance" between adjacent structures. The acoustic impedance of a tissue is related to its density; the greater the difference in acoustic impedance between two adjacent tissues the more reflective their boundary will be.

The frequency of the ultrasonic beams has an effect on both the image resolution and the penetration ability of the ultrasonic device. Higher frequency ultrasound waves have a longer near field (i.e., the region in the sound beam's path where the beam diameter decreases as the distance from the transducer increases) and less divergence in the far field (i.e., the region in the sound beam's path where the beam diameter increases as the distance from the transducer increases): higher frequency ultrasonic waves thus permit greater resolution of small structures. However, high frequency ultrasonic waves have less penetrating ability because their energy is absorbed and scattered by soft tissues. On the other hand, lower frequency ultrasonic waves have a greater depth of penetration, but the received images are much less well defined. The conventional frequency range for imaging human internal organs (using sound waves) is typically from about 3 MHz to about 5 MHz.

Two types of resolution generally apply to ultrasound imaging transducers: lateral resolution and axial resolution. Lateral resolution is the ability to resolve objects side by side and, as discussed above, is proportionally affected by the frequency (the higher the frequency, the higher the lateral resolution). Higher frequency transducers are used for infants and children because there is less need for deep penetration and the smaller structures can be viewed with greater lateral resolution. Lower frequencies are used for adults where the internal structures are larger and there is a greater need for depth penetration. Of course, when determining the appropriate frequency to be used, the structure, tissue, or organ to be viewed (and the exact purpose of the imaging) can matter more than the age of the subject. For example, diagnostic breast imaging on an adult may require a frequency of about 7 MHz or higher.

Axial resolution is the ability to resolve objects that lie one above the other. Because this is related to depth penetration, axial resolution is inversely proportional to the frequency of the transducer (depending on the size of the patient). In large patients, higher frequency beams are rapidly absorbed by the objects closest to the transducer, thus reducing depth penetration and axial resolution.

The focusing of an ultrasonic transducer can be implemented in one of two ways: mechanical or electronic. Mechanical focusing consists of placing an acoustic lens on the surface of the transducer or using a transducer with a concave face. One or several piezoelectric elements are used. In order to create a sweeping beam for 2D imaging, a single element may be oscillated back and forth, several elements may be rotated, or a single element may be used with a set of acoustic mirrors. This last transducer type (with the acoustic mirrors) is sometimes called the "wobbler" because of the vibration created as the mirrors rotate or oscillate inside the housing.

Figure 1:
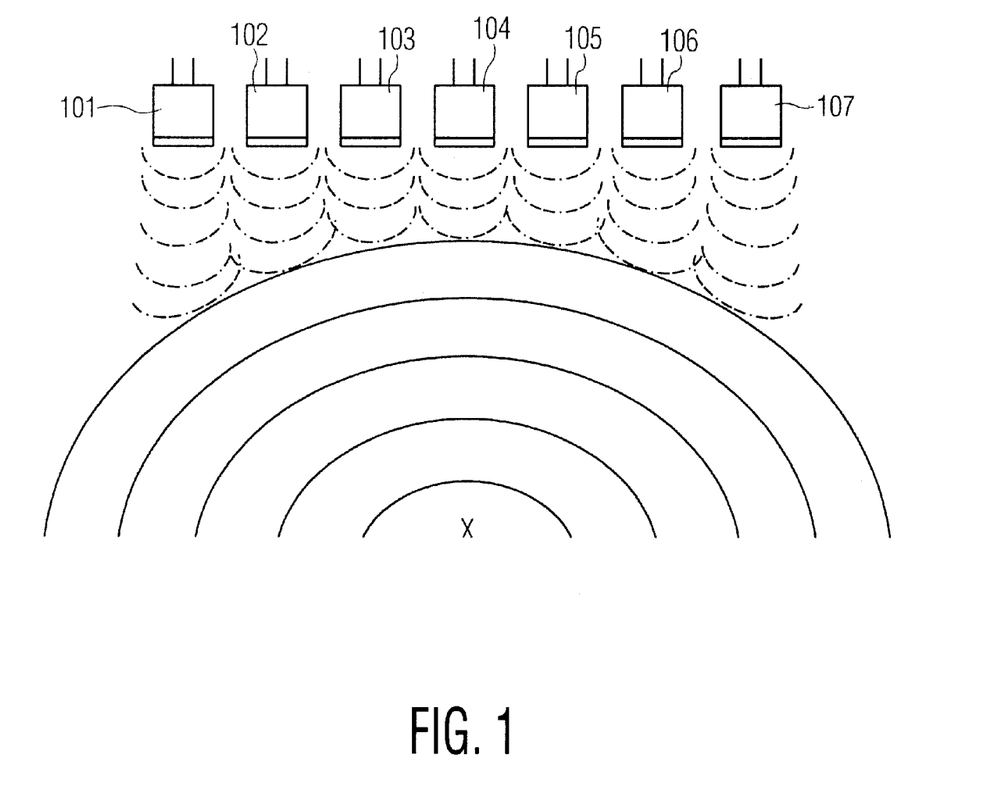
FIG. 1 shows how typical ultrasonic beam is formed by a linear array of piezoelectric elements.

Electronic focusing uses a process called phased array, where multiple piezoelectric elements in an array are stimulated (or "fired") sequentially in order to form and focus the beam. In an annular array, circular or ringlike elements and/or arrays are used. In a linear array, a row of elements is used to form and focus the beam. A transducer contains an array of transmitting elements and a similar array of receiving elements. An example of how a linear array forms and focuses a sound beam is shown in FIG. 1. In order to focus at point X, the outer elements 101 and 107 fire first, then elements 102 and 106, then elements 103 and 105, and finally element 104. As shown in FIG. 1, the resulting wavefronts combine to form a semicircular ultrasonic pulse whose focal point is X. By varying the sequential pattern of firing, the distance of focal point X from the transducer can be changed. Furthermore, varying the sequential pattern of firing can also be used to steer the beam. Steering is used to move focal point X left and right in FIG. 1. By rapidly steering a series of beams from left to right, a 2D cross-sectional image may be formed.

In 2D mode, one sweep from left to right is a frame, and the number of sweeps in a second is the frame rate (or fps—frames per second). Conventional frame rates ranges from about 12 fps to about 30 fps. The number of beams formed over time is the Pulse Repetition Frequency (PRF), measured in pulses per second. The range of PRFs for most commercial echocardiographs is between about 200 and about 5000 pulses per second. PRF varies with the type of imaging being performed. Most of the time spent in each second is used waiting for the echoes to return to the receiving elements in the transducer. In other words, after a beam is formed, the transmitting elements lie dormant while the beam travels to the various objects and then some of that sound energy returns (as echoes) to the transducer's receiving elements. The amount of time that the transmitting elements are transmitting sound energy is called the duty factor. Most transducers are acting as a receiver about 99% of the time, in which case the duty factor is 1 (%).

Aperture is the size of the active transmitting and receiving portion of a transducer array. Aperture is measured in square centimeters and is a function of the number of transducer elements used simultaneously to form an image. A common measurement of aperture size is F-number or F#, which is defined as the ratio of depth to aperture. These values are related to the lateral resolution (LR) by the following function:

$$LR = \lambda * F\# = \lambda * \frac{D}{A}$$

where $\lambda$=wavelength of sound pulse
D=depth of the scan
A=aperture of the scan As can be seen from the above equation, for a fixed frequency, the aperture size must increase as the scanning depth increases in order to maintain uniform lateral resolution throughout the image. Many ultrasonic systems select a transmit aperture based on the scan depth setting and continuously vary the reception aperture. It is desirable to achieve low F#s, which, because the scanning depth is limited by the position of the desired subject, is identical to seeking larger aperture sizes. It is also desirable to seek small wavelengths, which is equivalent to seeking higher frequencies.

There are a number of modes in which an ultrasonic transducer operates. The basic modes are A Mode, B Mode, M Mode, and 2D Mode. The A Mode is amplitude mode, where signals are displayed as spikes that are dependent on the amplitude of the returning sound energy. The B Mode is brightness mode, where the signals are displayed as various points whose brightness depends on the amplitude of the returning sound energy. The M Mode is motion mode, where B Mode is applied and a strip chart recorder allows visualization of the structures as a function of depth and time; The 2D Mode is two-dimensional (imaging) mode, where B Mode is spatially applied by sweeping the beam (as described above) so that structures are seen as a function of depth and width.

2D Mode refers to the most basic, fundamental imaging mode. There are other imaging modes, which also image in two dimensions (in three dimensions in some new technologies), but these are referred to by their own names, usually based on the type of technology/methodology used to produce the image. Some of these other imaging modes will be described below. When the term 2D (or "fundamental") Mode is used, it only refers to the basic spatially oriented B Mode, and not all two dimensional imaging modes. This application is concerned mostly with the imaging modes of an ultrasonic system; however, the inventive system and method could be applied to the other visualization modes as well.

There have been various solutions to the problem of higher frequency-greater resolution-less depth penetration and lower frequency-lower resolution-greater depth penetration. One solution is to use high frequency ultrasonic waves while boosting the power to a higher level in order to increase depth penetration. Another solution is harmonic imaging. With conventional imaging, the ultrasound system transmits and receives a sound pulse of a specific frequency (the "fundamental" frequency). As discussed above, parts of the sound pulse are reflected back to the transducer, where the reflected sound at the fundamental frequency is processed. In harmonic imaging, the transducer does not listen for the fundamental frequency, but for other frequencies—most notably, the "harmonic" frequency, which is twice the fundamental frequency (this is sometimes referred to as the "first harmonic"). To be more technically accurate, the transducer receives a signal comprised of a number of frequencies, including the fundamental and harmonic, and separates out the signal at the harmonic frequency (the "harmonic" for short). Once separated out, the harmonic is processed to produce an image.

Harmonics are generated by the object being imaged, either with or without the assistance of human intervention. When assisted, harmonics are generated by ultrasound "contrast agents" which are injected into the patient's body. These contrast agents generally contain very small bubbles which generate two kinds of echoes when struck by a pulse. First, the conventional echo is bounced back based on the fundamental frequency. But then the bubble vibrates (in response to the pulse), thereby generating a harmonic signal. Because these contrast agents are formed for the purpose of creating harmonic echoes (rather like a bell when struck by a clapper), very strong echoes are generated at the harmonic frequency, thereby producing excellent high contrast images.

When not relying on contrast agents, harmonic imaging uses the harmonics that are generated by the tissue of the body itself (having been "rung" by the ultrasonic pulse). Obviously, these harmonics do not generate as clear a picture as the harmonics from contrast agents. The ability to create harmonics in tissue varies depending on the tissue's location in the ultrasound beam's field of view. The most pronounced imaging effect is from harmonics located at and around the focal point of the ultrasonic beam (i.e., midfield). No harmonics are generated by tissue in the near field, and the harmonics generated in the far field attenuate quickly after being produced.

Harmonic imaging has a number of advantages. The beam formed at the harmonic frequency is narrower and has lower side-lobes, thereby significantly improving grayscale contrast resolution. Furthermore, since the harmonics are generated inside the body, they only pass through the fat layer once, rather than twice.

Some other modes of imaging are dependent on the Doppler effect, the phenomena whereby the frequency of sound from an approaching object has a higher frequency and, conversely, sound from a receding object has a lower frequency. In ultrasonic systems, this effect is used to determine the velocity and direction of blood flow in a subject. Doppler techniques can also be used with ultrasonic transducers which operate in continuous wave mode (i.e., part of the transducer array transmits while another part simultaneously receives).

Pulsed wave Doppler effect techniques have proven to be very accurate in blood flow studies. However, if the velocity of the blood flow being measured exceeds the Nyquist Limit (half the PRF), the ultrasonic readings become inaccurate. Most Doppler techniques try to achieve a high a PRF as possible in order to avoid this effect. One type of imaging, Color Flow Imaging or CFI, uses this effect (called "aliasing") to detect flow disturbances, e.g., transitions from laminar to turbulent flow. In CFI, multiple sample volumes are detected and displayed utilizing color mapping for direction and velocity flow data. Common mapping formats are BART (Blue Away, Red Towards), RABT (Red Away, Blue Towards), or enhanced/variance flow maps where color saturations indicate turbulence/acceleration and color intensities indicate higher velocities. Some maps use a third color, green, to indicate accelerating velocities and turbulence.

It is desirable for the ultrasonic system to operate at the highest frequency (for the reasons discussed above) and at the maximum acoustic intensity. Maximizing the acoustic intensity increases imaging performance by increasing the depth penetration and maximizing the signal to noise ratio (SNR). However, higher frequencies and greater acoustic intensities cause the ultrasonic transducer to heat up, and there are regulatory limits (and practical limits) on the surface temperature of an ultrasonic probe when interacting with a subject. Specifically, the upper temperature limit on the patient contact surface of an ultrasonic transducer is generally considered to be about 41° C. or about 16° C. above ambient temperature.

The heat of the transducer surface is generated both by the electroacoustic energy conversion process taking place in the transducer's piezoelements and by the acoustic energy passing through and/or into adjacent transducer materials (and the patient herself). Different methods and systems have been developed to deal with the heating problem and they can be broken into two types: active and passive.

Passive solutions use passive cooling mechanisms, i.e., spreading out the dissipated heat to as large an external transducer surface area as possible. Typically, the heat generated by the transducer array is absorbed by solid thermal conductors, and then this captured heat is moved by thermal convection into the transducer's external case, where it can dissipate in the atmosphere. Ideally, the external heat-convecting surface area would consist of the transducer's entire external surface area.

Figure 2:
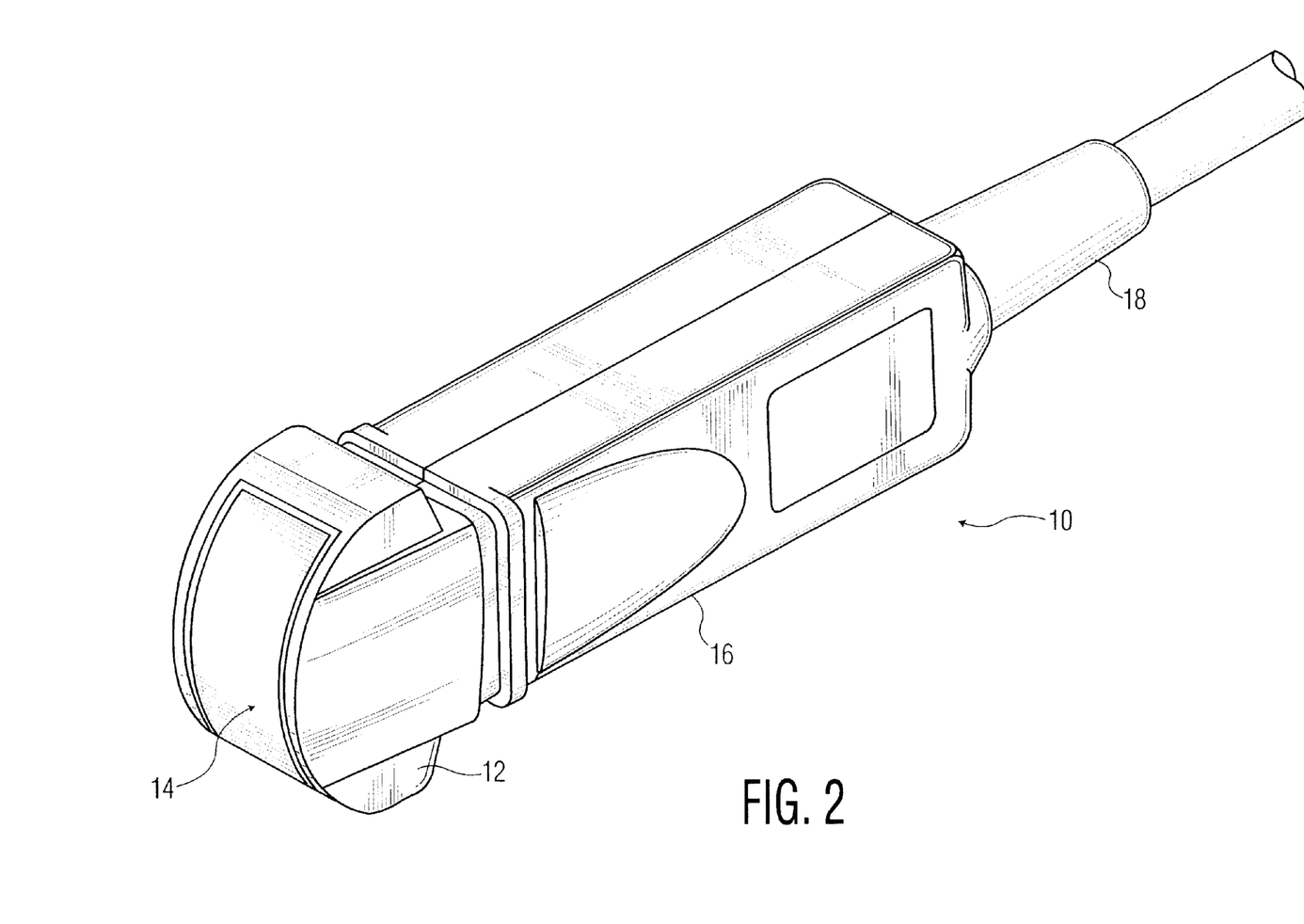
FIG. 2 shows a prior art ultrasonic transducer probe.

One example of a passive heat dissipation system is U.S. Pat. No. 5,213,103 ('103 patent), which is hereby incorporated by reference in its entirety. FIG. 2 shows the outside of the transducer in the '103 patent. A heat sink device (internal to the transducer, thus not shown) placed inside the transducer 10 behind the piezoelectric elements in the face 14 (i.e., the patient contact surface) on the head 12 of transducer 10. The heat sink extends the entire length of the transducer and conducts heat away from face 14, through head 12, to the sides of handle 16 and power cable 18. Heat conductive epoxy is used both to attach the heat sink to the transducer housing and to conduct the heat from the heat sink to the transducer housing.

Another example of a passive heat dissipation system is U.S. Pat. No. 5,555,887 ('887 patent), which is hereby incorporated by reference in its entirety. The '887 patent applies heat dissipation to an endoscopic ultrasound transducer by embedding aluminum foil in acoustic lens material in front of the transducer array. Heat is conducted by the aluminum foil to a heat sink positioned at a distance from the patient contacting surface of the probe. U.S. Pat. No. 5,721,463 ('463 patent), which is hereby incorporated by reference in its entirety, describes a passive heat dissipation system which uses a bundle of coaxial cables to vent heat away from the face of the probe.

These passive heat sinks are effective, but they also add to the transducer's overall thermal dissipation resistance. The fundamental limitation is that, for most transducers, even if heat is spread uniformly on the external case surfaces, it only takes a few watts of transducer driving power to cause the average transducer surface temperature to become unacceptable either with respect to the patient or the sonographer. In these cases, and particularly for small transducers having small surface areas, one may find that one is unable to operate at the allowable acoustic intensity limit because of excessive temperatures.

Active solutions, on the other hand, use active cooling means, such as circulating coolant systems. One example, U.S. Pat. No. 5,560,362 ('362 patent), which is hereby incorporated by reference in its entirety, describes a heat dissipation system in which a pumping or pressurization means actively circulates a gaseous or liquid coolant in a cable, part of which is nearby the transducer array. The system can be a single pass, multipass, or closed loop circulating system, and the coolant may pass through a heat exchanger, a heat pipe, a thermoelectric cooler, an evaporator/condenser system, and/or a phase change material.

An ultrasonic transducer cooling system which uses feedback control is shown in U.S. Pat. No. 6,210,356 ('356 patent), which is hereby incorporated by reference in its entirety. The '356 patent is directed to a catheter which provides ultrasonic energy (and perhaps medicine) as a therapeutic treatment to a site inside a patient's body. Thus, no imaging or sensing is being performed by the ultrasonic transducer in the '356 patent. Temperature sensors are positioned in the surface coating of the catheter next to the ultrasound transducer in order to provide a measure of the temperature on the exterior surface of the catheter. This measure is used as a feedback control signal for the power circuits of the ultrasonic transducer. After the user sets a predetermined temperature, the power circuits decrease or increase power in the same proportion as the measured temperature is above or below the predetermined temperature.

The device described in the '356 patent also includes safety control logic which detects when the temperature at a temperature sensor has exceeded a safety threshold. When this occurs, the power circuits stop providing power to the ultrasonic transducer. However, such a feedback control system can be inappropriate for ultrasonic imaging/measuring applications.

Although abruptly turning off the power during a therapeutic ultrasonic session may not be damaging, abruptly turning off the power during an imaging/measuring session can be potentially dangerous (e.g., a sudden blackout during a surgical procedure). Even when not dangerous, turning off the image makes the diagnosis and analysis of image data difficult. Thus, there is a need for a system and method for reducing the temperature of the ultrasonic transducer in general, and the patient contacting surface in specific, which does not merely turn the transducer off. Furthermore, there is a need for a system and method which may work either as a replacement for the conventional active or passive heat dissipation systems or as an adjunct to them.

SUMMARY OF THE INVENTION

One object of the present invention is to provide a system and method for reducing the temperature of an imaging ultrasonic transducer in general, and the patient contacting surface in specific, without merely turning the transducer off.

Another object of the present invention is to provide a system and method for reducing the temperature of an imaging ultrasonic transducer which may work either as a replacement for the conventional active or passive heat dissipation systems or as an adjunct to them.

These and other objects are achieved by the present invention in which a system and method control the temperature of an imaging ultrasonic transducer by alternating a high power intensity imaging mode and a lower power intensity imaging mode. The present invention has two aspects: 1) switching from one imaging mode to another; and 2) cycling rapidly between imaging modes (and combining the data to create a single image). In some embodiments, feedback from temperature sensors in the ultrasonic transducer is used to control the switching. In other embodiments, switching is performed based on how much time has elapsed. In yet other embodiments, the operator controls when the imaging modes are switched.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

DETAILED DESCRIPTION OF THE PRESENTLY PREFERRED EMBODIMENTS

The present invention is directed to a novel system and method of controlling the radiant heat from the patient contact surface of an ultrasonic transducer. Although the details of implementation may be different in different embodiments, the present invention is not limited to any particular type of ultrasonic transducer, whether used internally or externally, or any particular mode of imaging and/or data analysis. The presently preferred embodiments of the present invention control the temperature of the transducer face by alternating the imaging modes of the system based on feedback from temperature sensing elements placed in the transducer. In one preferred embodiment, the system switches from a higher power imaging mode to a lower power imaging mode when a threshold temperature is reached. In another preferred embodiment, the system switches to a "mixed" imaging mode, where the system cycles between a higher power imaging mode and a lower power imaging mode.

Figure 3:
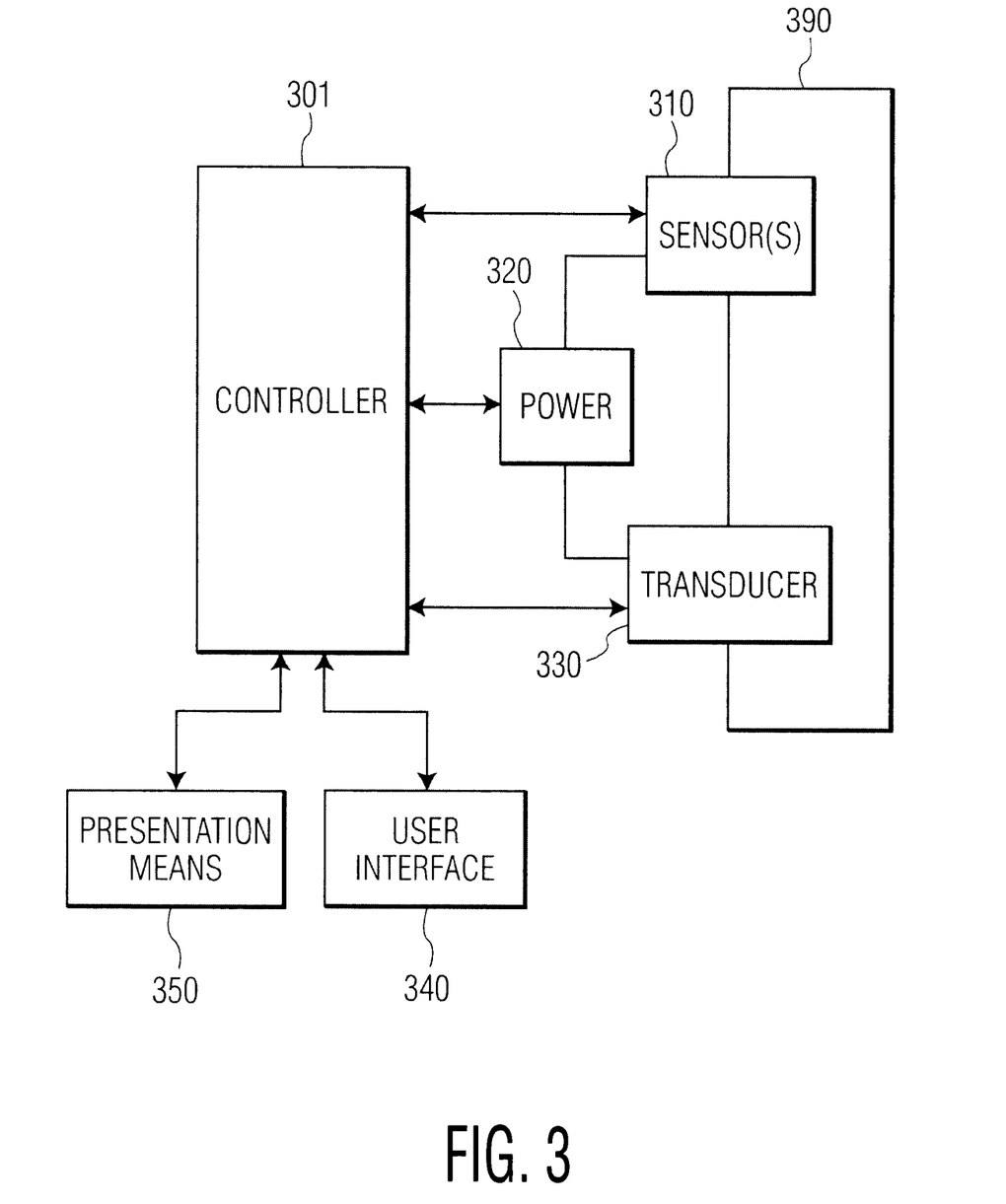
FIG. 3 is a block diagram showing the functional modules of an ultrasonic transducer system according to a preferred embodiment of the present invention.

A block diagram of the functional modules in a preferred embodiment of the present invention is shown in FIG. 3. Each of the functional modules should be understood as an abstraction of the function or combination of functions named, and each can be combined or further divided as necessary for implementing a particular embodiment. These functions may be implemented in software, hardware, or a combination of the two.

In FIG. 3, a controller 301, which may take the form of a microprocessor, controls the overall functioning of the ultrasonic device. Controller 301 receives measurement signals from temperature sensor(s) 310. Possible temperature sensors include any known conventional temperature sensor, such as, for example, thermistors, thermocouples, resistance temperature detectors (RTDs), and fiber optic temperature sensors which use thermalchromic liquid crystals. There may be one or more temperature sensor(s) 310, and their appropriate placement within the ultrasonic system will depend on the use and type of system, as would be known to one skilled in the art. In the preferred embodiments, the appropriate placement of the temperature sensor(s) 310 is the most suitable location to ascertain the surface temperature of the patient contacting surface 390 of the ultrasonic transducer.

Power supply 320, under control of controller 301, supplies power to the various components of the ultrasonic system. For example, controller 320 controls the amount of power sent to the ultrasonic transducer 330. Ultrasonic transducer 330 is also under the control of controller 301. The present invention is not limited to any particular type of imaging ultrasonic system, nor to any particular imaging or non-imaging mode. User interface 340 allows the user to monitor the condition of, and/or to interact with, the ultrasonic system; it may comprise a keyboard (and mouse), a microphone (and voice recognition software), a handheld input device, or any other form of input device compatible with the present invention. Presentation means 350 is for presenting system parameters, and may or may not be used to see the results of the ultrasonic testing being performed. Presentation means 350 may comprise a display monitor, a speaker (with either voice synthesis or pre-recorded speech), or any other means of presenting the status of system parameters and/or allowing the user to interact with the ultrasonic system.

Although not necessary, an ultrasonic system according to the present invention may also comprise a passive or active heat dissipation system. In some embodiments of the present invention, the present invention itself acts as the sole heat dissipation system for the ultrasonic transducer.

Figure 4:
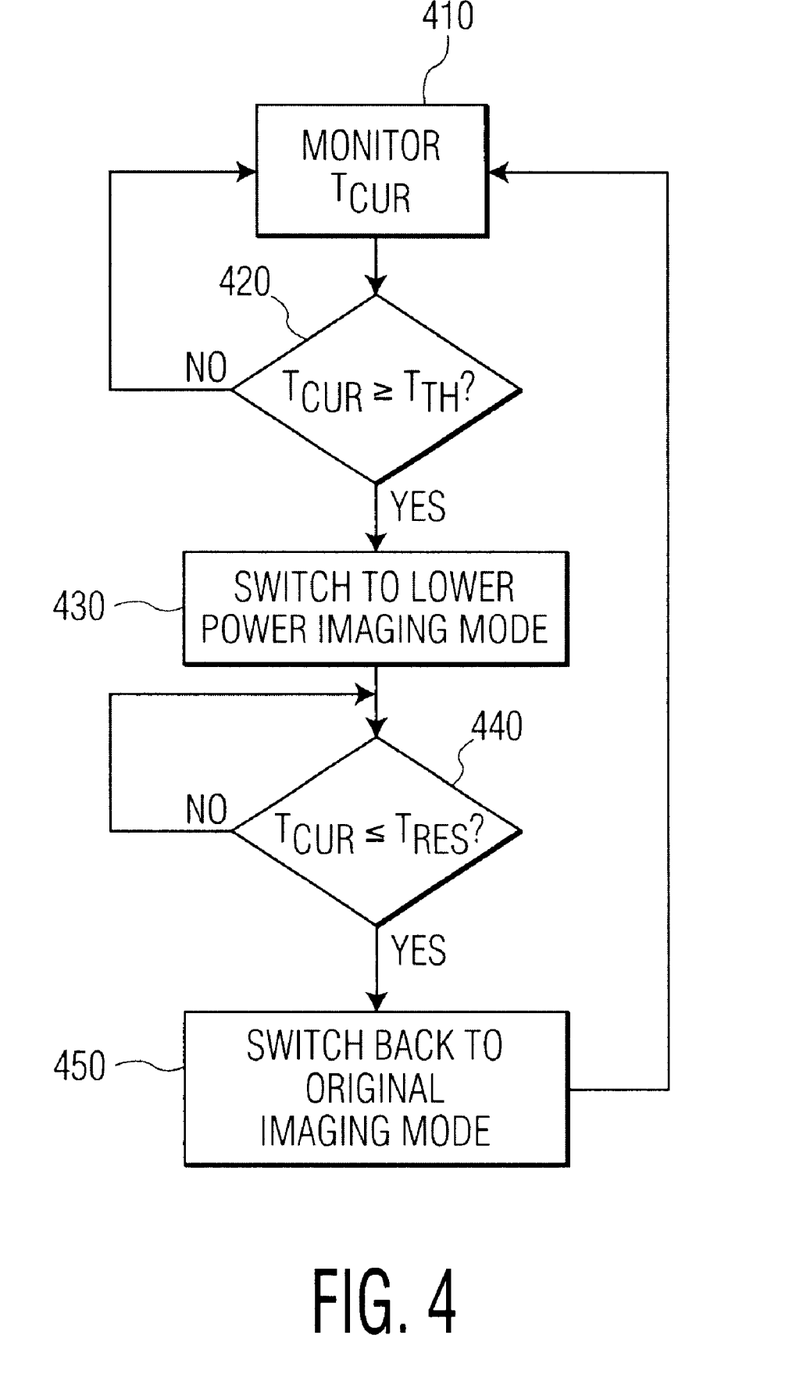
FIG. 4 is a flowchart of an overheating prevention method according to a preferred embodiment of the present invention in which the imaging mode is reset when the temperature has cooled to a certain point.

An imaging ultrasonic system temperature control method according to a preferred embodiment of the present invention is shown in FIG. 4. In step 410, the current temperature $T_{cur}$ of the patient contacting surface 390 of the ultrasonic transducer 330 is monitored by controller 301. An example of a system which uses such feedback is described in the U.S. patent application Ser. No. 10/268,261 entitled "Imaging Ultrasound Transducer Temperature Control System and Method using Feedback", filed on Oct. 10, 2002 and assigned to the same assignee as the present application. The aforementioned patent application is hereby incorporated by reference. In step 420, it is determined whether the current temperature $T_{cur}$ has exceeded a threshold temperature $T_{th}$. The threshold temperature $T_{th}$ may be any temperature under (or equal to) the critical temperature $T_{crit}$ at which discomfort or damage may occur to the patient. Obviously, in embodiments where $T_{th}$ equals the critical temperature $T_{crit}$ the assumption is that the subsequent steps will reduce the temperature so quickly that no discomfort will come to the patient. In some embodiments, the operator may select the threshold temperature $T_{th}$ and/or the critical temperature $T_{crit}$. In other systems, they may be predetermined.

If the current temperature $T_{cur}$ is below the threshold temperature $T_{th}$ in step 420, the system returns to monitoring step 410. On the other hand, if the current temperature $T_{cur}$ is greater than, or equal to, the threshold temperature $T_{th}$, in step 420, the system switches from the imaging mode that it is currently in to a lower power imaging mode in step 430. As an example, if the system was currently in harmonic imaging mode, it would switch to a lower power imaging mode, such as fundamental (2D) imaging. Because of the lower power generated in this mode, the ultrasonic transducer does not become as hot, and will be able to cool from the high temperature caused by the high power imaging mode that the system was previously in.

After the imaging mode has been changed in step 430, the system determines whether it should be reset back to the higher power imaging mode. In this embodiment, the system will be reset when it reaches a reset temperature $T_{res}$ which is below threshold temperature $T_{th}$. The reset temperature $T_{res}$ could be the optimal operating temperature of the ultrasonic transducer. In step 440, it is determined whether the current temperature $T_{cur}$ is below (or equal to) the reset temperature $T_{res}$. If it is, the system changes the imaging mode back to the original higher power imaging mode in step 450, and then returns to monitoring the temperature in step 410. If the temperature has still not lowered to the reset temperature $T_{res}$, the system stays in a monitoring loop (repeating step 440), waiting for the current temperature $T_{cur}$ to become sufficiently lowered to return to the higher power imaging mode.

Figure 5:
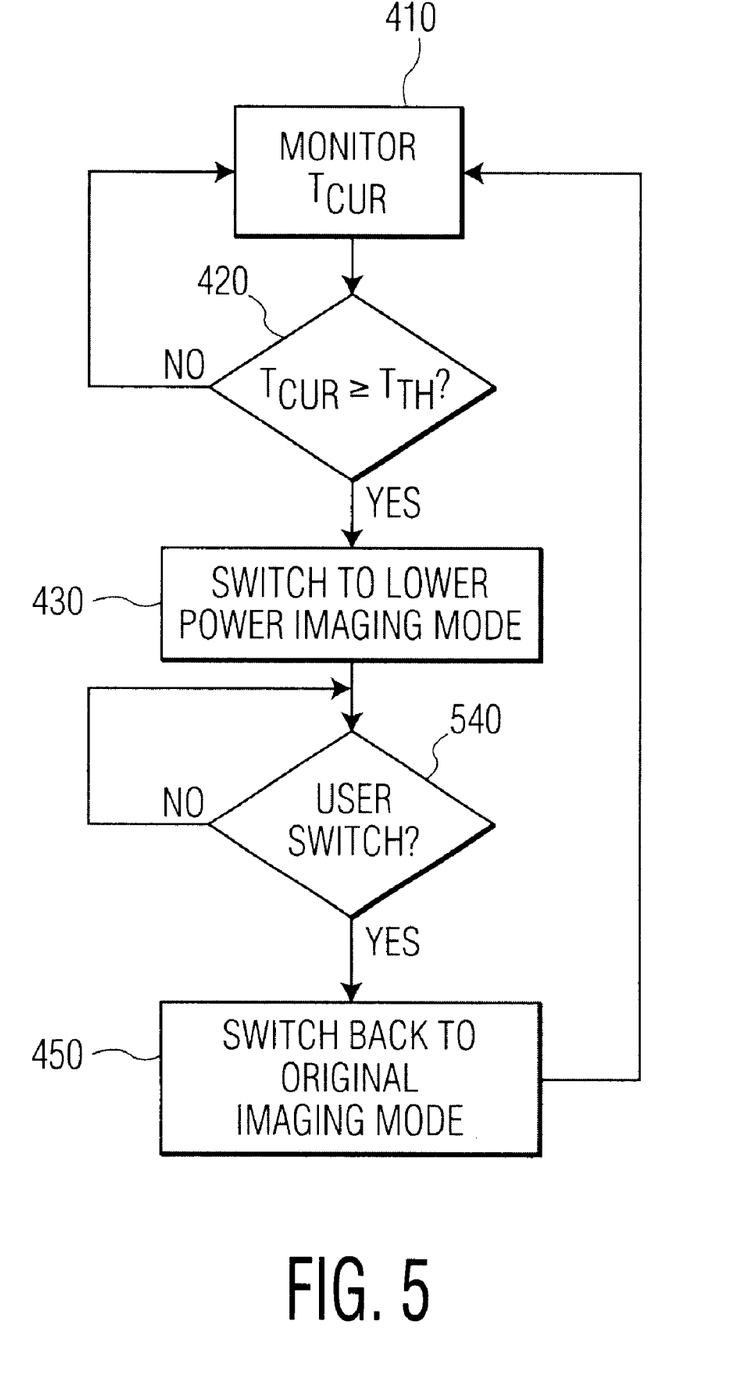
FIG. 5 is a flowchart of an overheating prevention method according to another preferred embodiment of the present invention in which the imaging mode is reset by the user.

In FIG. 5, a preferred embodiment very similar to the embodiment in FIG. 4 is shown, but the preferred embodiment of FIG. 5 has a different manner of resetting to the higher power imaging mode. The preferred embodiment of FIG. 5 allows the user to reset the system back to the higher power imaging mode. Specifically, steps 410–430 in FIG. 5 are the same as FIG. 4, but once the system is in the lower power imaging mode, it waits for the user to indicate that he or she wishes to return to the higher power imaging mode in step 540. In such an embodiment, it is preferable that the user has both the ability to switch back to the higher power imaging mode and the ability to switch out of the higher power imaging mode (to the lower power imaging mode). In this manner, the operator could avoid reaching threshold temperature $T_{th}$ by changing to a lower power imaging mode whenever the high power imaging mode is not necessary or when the operator ascertains that the temperature is getting too hot.

In some embodiments, the system does not reset at all, but remains using the lower power imaging mode until the session is over.

Figure 6:
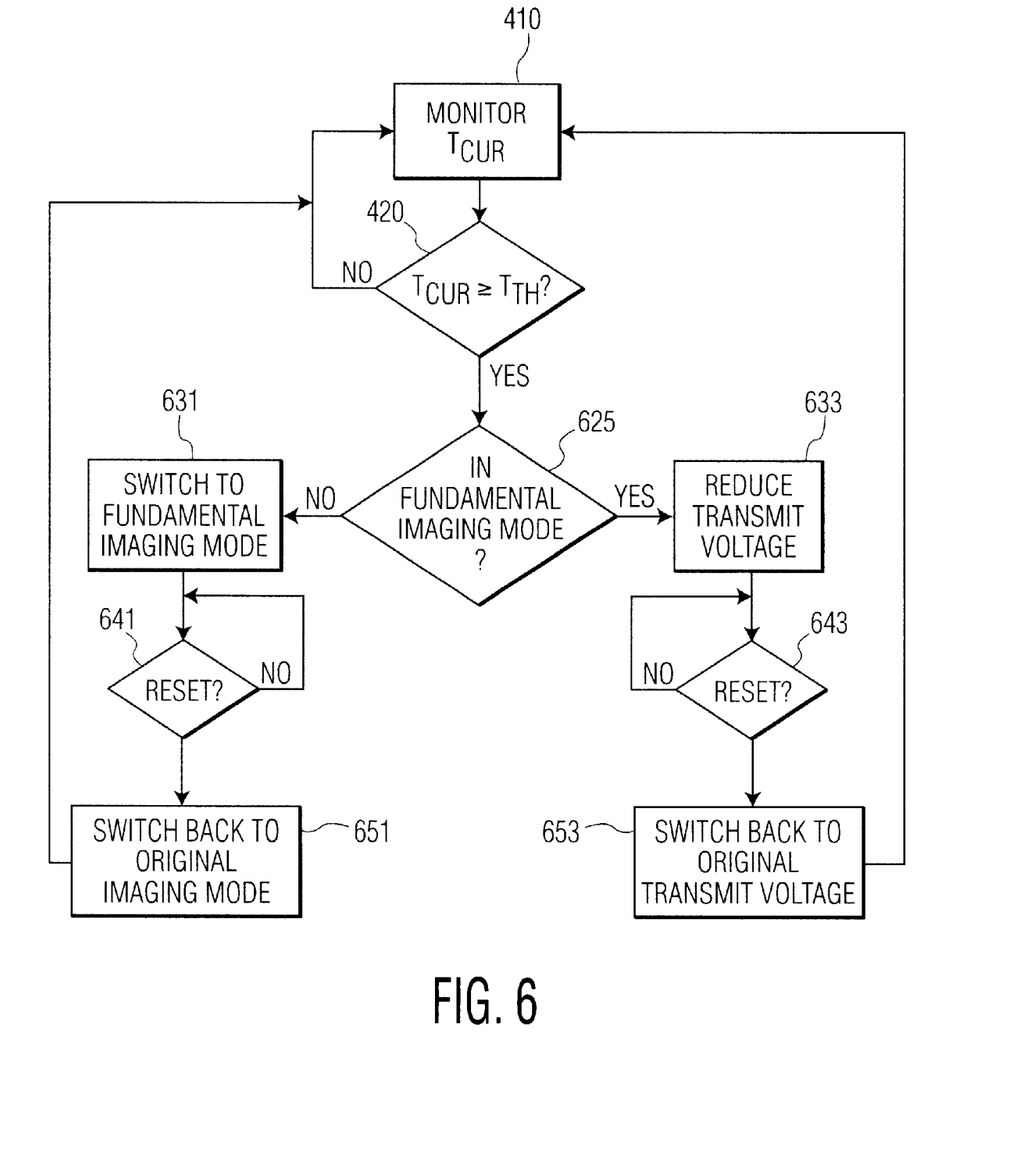
FIG. 6 is a flowchart of an overheating prevention method according to yet another preferred embodiment of the present invention in which the imaging mode is set to the fundamental imaging mode or, if already in the fundamental imaging mode, the transmit voltage is reduced.

In FIG. 6, a preferred embodiment of the present invention is shown where, once the threshold temperature $T_{th}$ is reached, the system defaults to the fundamental imaging mode. If the system is already in the fundamental imaging mode, the system reduces the transmit voltage in order to reduce the temperature of the ultrasonic transducer. FIG. 6 starts with the temperature monitoring step 410, and step 420 where it is determined if the current temperature $T_{cur}$ is greater than, or equal to, the threshold temperature $T_{th}$. If the current temperature $T_{cur}$ is less than the threshold temperature $T_{th}$ in step 420, the system continues monitoring by returning to step 410.

If the current temperature $T_{cur}$ is greater than, or equal to, the threshold temperature $T_{th}$ in step 420, it is determined whether the system is currently in fundamental imaging mode in step 625. If the system is not in fundamental imaging mode in step 625, the system switches to fundamental imaging mode in step 631. After step 631, the method enters a loop where it checks if it can reset in step 641. In this context, the <RESET?> step covers any manner of resetting the original mode. Thus, step 641 could be the automatic temperature checking of step 440 in FIG. 4, the user-controlled reset of step 540 in FIG. 5, or any other type of reset mechanism. If the system is ready to reset in step 641, it switches back to the original imaging mode in step 651 and returns to monitoring step 410.

If the system is in fundamental imaging mode in step 625, the system reduces the transmit voltage in step 633. After step 633, the method enters a loop where it checks if it can reset in step 643. Like step 641, step 643 can be any type of reset mechanism. If the system is ready to be reset in step 643, it switches back to the original transmit voltage in step 653 and returns to monitoring step 410.

Although the system reduces the transmit voltage in step 633 of FIG. 6, it is possible in other embodiments to change other ultrasonic system parameters in order to reduce the ultrasonic transducer temperature. These system parameters include, but are not limited to: the duty cycle (the system will reduce the amount of time the transmitting piezoelectric elements are active during each transmit-receive cycle), frequency (the system decreases the frequency of the ultrasonic sound waves), frame rate (the system decreases the frame rate, i.e., number of sweeps per second), Pulse Repetition Frequency (PRF—the system decreases the number of beams formed per second), aperture (the system decreases the size of the aperture), imaging depth (the system decreases the scanning depth), and/or sector width (the system decreases the width of the zone being scanned).

Figure 7:
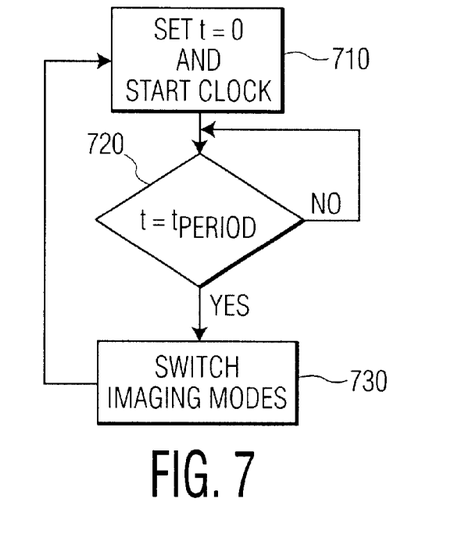
FIG. 7 is a flowchart of an overheating prevention method according to still another preferred embodiment of the present invention in which the imaging mode is switched periodically.

FIG. 7 shows another preferred embodiment of the present invention. In FIG. 7, the system does not use feedback from temperature sensors in the ultrasonic transducer, but rather attempts to maintain a low average transducer temperature by periodically switching between imaging modes (i.e., between an higher power imaging mode and a lower power imaging mode). In step 710, the session begins with the clock being set to zero (t=0). Then, the system waits for one period $t_{period}$ to complete in step 720. When a period ends, the system switches imaging modes in step 730. This system keeps the ultrasonic transducer at a lower temperature by not maintaining a higher power imaging mode for too long. In another embodiment, the time periods for the different imaging modes could be unequal. For example, the time period $t_{per-harmonic}$ for maintaining the harmonic imaging mode could be greater than time period $t_{perfundamental}$ for maintaining the fundamental imaging mode. This would allow the operator to have a preferred imaging mode for longer periods of time.

Furthermore, using a time period for remaining in the lower power imaging mode can be used in any of FIGS. 4–6. In other words, rather than having, for example, the user switch back the imaging mode, the imaging mode would switch back after a predetermined period of time.

In some embodiments, the manner in which the imaging modes are changed is predetermined, i.e., they are hardwired in the device itself. In other words, while in color flow imaging mode, the system would be programmed to switch to the fundamental imaging mode. In another embodiment, the operator selects the manner in which the imaging modes are changed before the ultrasonic session begins; in another, the operator selects the manner in which the imaging modes are changed during the ultrasonic session. An example of a system in which the user has such control is described in the U.S. patent application Ser. No. 10/269,144 entitled "Operator Supervised Temperature Control System and Method for an Ultrasound Transducer", filed Oct. 11, 2002 and assigned to the same assignee as the present application. The aforementioned patent application is hereby incorporated by reference.

Figure 8:
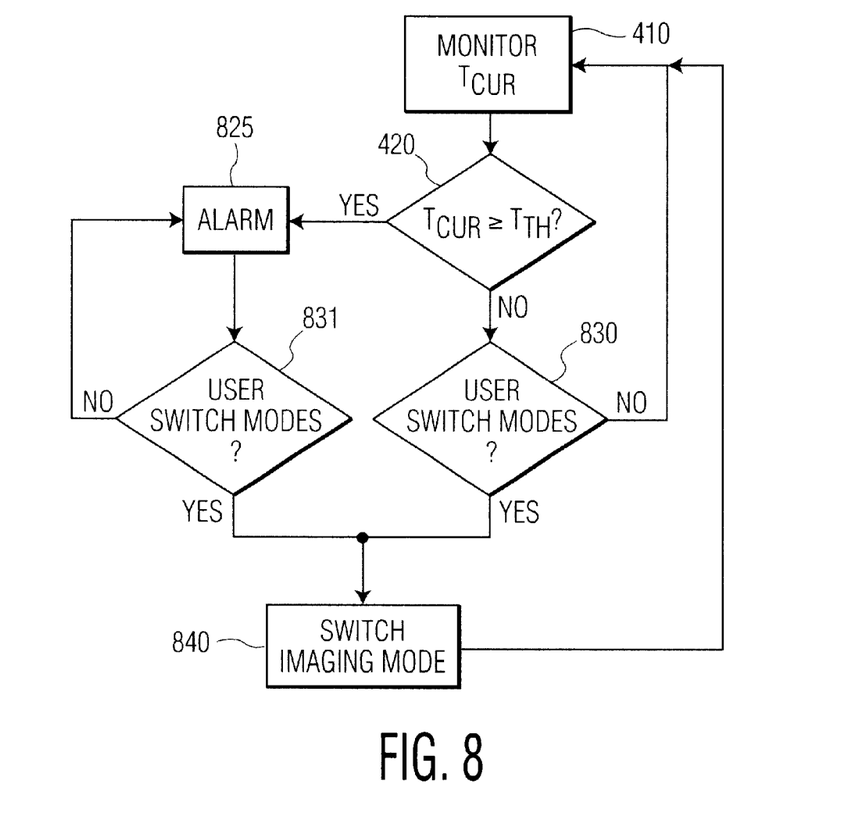
FIG. 8 is a flowchart of an overheating prevention method according to yet another preferred embodiment of the present invention in which the imaging mode is set by the operator.

In the embodiment shown in FIG. 8, the operator controls when the imaging mode is changed, i.e., the operator monitors the temperature and other parameters of the ultrasonic system and interacts directly with the system in order to change the imaging mode before the temperature reaches a critical point.

In FIG. 8, the system is monitoring the transducer temperature in step 410, as in the other embodiments. This measured temperature is shown on a display so that the operator may monitor the temperature and act to change the imaging mode before the temperature is too high. Besides the current temperature of the patient contacting surface, other system parameters, such as the current rate of heating, could be displayed on the monitor. This information could be displayed in a variety of ways: as gauge icons, as digital readouts, as histograms, or any other manner of indicating a quantity on a screen. Other system parameters to display include the applied voltage, the current imaging mode of the system, the frame rate, the sector width, etc. In addition, the display may show the time left before the transducer reaches the critical temperature so that the operator may correctly determine the correct time to change the imaging mode.

Just in case the operator is distracted, it is determined if the current temperature $T_{cur}$ has reached the threshold temperature $T_{th}$ (which indicates that the operator should act before the transducer reaches the critical temperature) at step 420. An alarm is issued in step 825 if the temperature has reached this threshold. This alarm may take any form; for example, it may appear has a bright red flashing blip on the display. After the alarm has gone off in step 825, the system checks to see if the user has indicated a desire to switch modes in step 831. If not, the alarm continues in step 825. If the user does initiate switching modes in step 831, the indicated imaging mode is switched to in step 840.

If the temperature is below the threshold in step 420, the system checks to see if the user wishes to change the current imaging mode in step 830. If not, the method returns to monitoring step 410. Because the user may change imaging modes at any point during a session, the system shown in FIG. 8 is continually checking to see if the user wants to change a parameter in the loop consisting of steps 410, 420, and 830. This, as all other steps or procedures in these exemplary embodiments, can be implemented a number of ways. For instance, the system may not be actually "checking" periodically if the user has indicated a desire to change imaging modes. There might be a physical button, or a virtual button shown on the display (and clicked by using the interface), which causes another display showing the possible imaging modes to which the operator can switch. For example, a virtual button labeled "Change imaging mode?" may be permanently displayed in the corner of the display screen, waiting for the user to click it.

The other aspect of the present invention provides for cycling rapidly between imaging modes in order to cool down the ultrasonic transducer. This overheating prevention method consists of "mixing" a high power imaging mode with a lower power imaging mode so that the overall transmit power (and therefore heating) will be reduced. This mixed mode is compatible with any of FIGS. 4–8, i.e., rather than switching to a lower power imaging mode, the system switches into mixed imaging mode.

As stated above, mixed imaging mode is when the ultrasonic transducer operates by switching (or cycling) between a higher power imaging mode, such as harmonic imaging, and a lower power imaging mode, such as fundamental (2D) imaging. The various parameters of this switching, e.g. the time period for each mode, the transmit power for each mode, etc., may be selected by the operator or set by the system itself. The manner in which the images formed from the two different imaging modes are combined in order to present to the user can take a variety of forms. Examples of display formats include: alternating frames, alternating scan lines, or compound image. In the alternating frames format, the display alternates frames between images based on harmonic imaging and images based on fundamental imaging. This mixed format produces a flickering appearance, which is not too distracting because the overall effect of the image is as if it was being illuminated by different lighting (not simply alternating bright and dim illumination). This mixed format can be assisted by automatically adjusting the brightness of the harmonic image to that of the fundamental image.

In the alternating scan lines format, every other line in the scanned plane is scanned with the harmonic image. The resulting combined image is displayed with the regular display averaging which is used to smooth and fill in scan lines. This averaging smoothes the appearance of the image. In the compound image format, a compound image is formed by displaying a central harmonic image of limited width and filling out the edges of the sector with the low power, fundamental mode image.

In general, the present invention has two aspects: switching between imaging modes and cycling between imaging modes (and combining the data to create a single image). However, the present invention is in no way limited to the exemplary embodiments described above and more complex methods are contemplated. As one example, although 3D imaging is not explicitly discussed, the present invention could be easily applied to 3D imaging. As another example, any of the exemplary methods above could be modified by the addition of extra steps in which the ultrasonic transducer is turned off once the critical temperature $T_{crit}$ (at which patient discomfort or damage may occur) is reached. As yet another example, various levels of threshold alerts could also be generated as the ultrasonic transducer temperature comes closer to the critical temperature $T_{crit}$. Furthermore, any of the steps in the exemplary embodiments could replace steps in another exemplary embodiment, or be used in addition to the steps in another exemplary embodiment.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A method of cooling an imaging ultrasonic transducer in an imaging ultrasonic transducer system, wherein a patient-contacting surface of said imaging ultrasonic transducer is pressed externally against the skin of a patient in order to generate an image, comprising the steps of:

monitoring a temperature of the imaging ultrasonic transducer; and automatically switching from a desired higher power imaging mode to a less desired lower power imaging mode based on the monitored temperature, if necessary to reduce the temperature of the patient contacting surface of the imaging ultrasonic transducer to prevent at least one of pain to the patient and damage to the skin of the patient caused by the temperature of the patient-contacting surface.

2. The method of claim 1, wherein the step of switching from a desired higher power imaging mode to a less desired lower power imaging mode comprises the step of:

automatically switching from a desired higher power imaging mode to a less desired lower power imaging mode if the monitored temperature is greater than, or equal to, a threshold temperature.

3. The method of claim 1, further comprising, after switching to the lower power imaging mode, the step of:
   switching back to the higher power imaging mode.

4. The method of claim 1, further comprising, after switching to the lower power imaging mode, the step of:
   automatically switching back to the higher power imaging mode.

5. The method of claim 4, wherein the step of automatically switching back comprises the step of:
   automatically switching back to the higher power imaging mode when the monitored temperature reaches a reset temperature.

6. The method of claim 4, wherein the step of automatically switching back comprises the step of:
   automatically switching back to the higher power imaging mode after a predetermined period of time has passed.

7. The method of claim 1, further comprising, after switching to the lower power imaging mode, the step of:
   switching back, by an operator, to the higher power imaging mode.

8. The method of claim 1, wherein the step of switching from a desired higher power imaging mode to a less desired lower power imaging mode comprises the step of:
   automatically switching from a current imaging mode to fundamental imaging mode if the monitored temperature is greater than, or equal to, a threshold temperature.

9. The method of claim 8, wherein, if the current imaging mode is the fundamental imaging mode when the monitored temperature is greater than, or equal to, a threshold temperature, said method further comprises the step of:
   changing at least one mutable system parameter so that the temperature in the patient contacting surface of the imaging ultrasonic transducer is reduced.

10. The method as recited in claim 9, wherein the at least one mutable system parameter comprises at least one of:
    duty cycle, wherein the duty cycle is a ratio of the time in which the imaging ultrasonic transducer is transmitting to the time in which the imaging ultrasonic transducer is receiving;
    applied voltage to a transmitting elements in the imaging ultrasonic transducer;
    frequency of a ultrasonic sound waves;
    frame rate of the imaging ultrasonic transducer;
    pulse repetition frequency (PRF) of the imaging ultrasonic transducer;
    aperture of the imaging ultrasonic transducer;
    imaging depth of the imaging ultrasonic transducer;
    sector width of the imaging ultrasonic transducer.

11. The method of claim 1, wherein the step of monitoring the temperature of the imaging ultrasonic transducer is performed by means of at least one temperature sensor positioned in the imaging ultrasonic transducer so that the temperature of the patient contacting surface can be ascertained.

12. The method as recited in claim 1, further comprising the steps of:
    determining by the imaging ultrasonic transducer system whether the monitored temperature of the imaging ultrasonic transducer is greater than or equal to a critical temperature;
    turning the imaging ultrasonic transducer off if it is determined that the monitored temperature is greater than or equal to the critical temperature; and
    once the imaging ultrasonic transducer has been turned off:
       determining the current temperature of the imaging ultrasonic transducer;
       determining whether the current temperature is less than the critical temperature; and
       turning the imaging ultrasonic transducer back on if it is determined that the current temperature is less than a reset temperature.

13. An ultrasonic imaging system which performs the steps of claim 1.

14. A method of cooling an imaging ultrasonic transducer in an imaging ultrasonic transducer system, wherein a patient-contacting surface of said imaging ultrasonic transducer is pressed externally against the skin of a patient in order to generate an image, comprising the steps of:
    automatically switching from a desired higher power imaging mode to a less desired lower power imaging mode after a predetermined period of time has elapsed;
    whereby at least one of pain to the patient and damage to the skin of the patient caused by the temperature of the patient-contacting surface of the imaging ultrasonic transducer are prevented.

15. An imaging ultrasonic system which performs the steps of claim 14.

16. A method of cooling an imaging ultrasonic transducer, wherein a patient-contacting surface of said imaging ultrasonic transducer is pressed externally against the skin of a patient in order to generate an image, comprising the steps of:
    cycling between a higher power imaging mode with a lower power imaging mode while operating the ultrasonic transducer;
    combining the data from the two different imaging modes; and
    presenting the combined data in a display for the ultrasonic transducer data;
    whereby said cycling between imaging modes prevents at least one of pain to the patient and damage to the skin of the patient caused by the temperature of the patient-contacting surface of the imaging ultrasonic transducer.

17. The method as recited in claim 16, wherein said combining and presenting steps comprise:
    alternating frames between data from the higher power imaging mode and data from the lower power imaging mode in the display.

18. The method as recited in claim 16, wherein said combining and presenting steps comprise:
    alternating scan lines between data from the higher power imaging mode and data from the lower power imaging mode in the display.

19. The method as recited in claim 16, wherein said combining and presenting steps comprise:
    forming a compound image by presenting a central image of limited width based on data from the higher power imaging mode and filling out the edges with data from the lower power imaging mode in the display.

20. The method of claim 16, wherein the higher power imaging mode is harmonic imaging and the lower power imaging mode is fundamental imaging.

21. An imaging ultrasonic system which performs the steps of claim 16.

* * * * *